United States Patent [19]

Samain

[11] Patent Number: 5,690,697
[45] Date of Patent: Nov. 25, 1997

[54] SET, PROCESS, AND DEVICE FOR DYEING KERATINOUS FIBERS WITH INDOLES OR INDOLINES AND MANGANESE SALTS AT SPECIFIC PH RANGES

[75] Inventor: Henri Samain, Bievres, France

[73] Assignee: L'Oreal, Paris, France

[21] Appl. No.: 504,744

[22] Filed: Jul. 20, 1995

[30] Foreign Application Priority Data

Jul. 22, 1994 [FR] France .................... 94 09118

[51] Int. Cl.$^6$ .................................................. A61K 7/13
[52] U.S. Cl. .................................... 8/423; 8/406; 8/628
[58] Field of Search ........................... 8/404, 406, 409, 8/423, 431, 435, 628

[56] References Cited

U.S. PATENT DOCUMENTS

| | | | |
|---|---|---|---|
| 5,131,911 | 7/1992 | Lang et al. | 8/423 |
| 5,173,085 | 12/1992 | Brown et al. | 8/423 |
| 5,368,610 | 11/1994 | Chan et al. | 8/423 |
| 5,413,612 | 5/1995 | Wenke | 8/423 |

FOREIGN PATENT DOCUMENTS 797174  6/1958  United Kingdom .......... 8/423

*Primary Examiner*—Paul Lieberman
*Assistant Examiner*—Caroline L. Dusheck
*Attorney, Agent, or Firm*—Finnegan, Henderson, Farabow, Garrett & Dunner

[57] ABSTRACT

A set for dyeing keratinous fibers, a dyeing composition, and a process for dyeing keratinous fibers using this dyeing composition are disclosed. Also disclosed is a multi-compartment device, or kit, one of the compartments of which contains the composition of the invention.

26 Claims, No Drawings

SET, PROCESS, AND DEVICE FOR DYEING KERATINOUS FIBERS WITH INDOLES OR INDOLINES AND MANGANESE SALTS AT SPECIFIC PH RANGES

The invention is directed to a new set for dyeing keratinous fibres, and in particular human keratinous fibres such as hair, a process for dyeing keratinous fibres using this set and a suitable dyeing kit. The invention is also directed to a new dyeing composition.

The dyes of the indole and indoline family are well known for their use in dyeing keratinous fibres, and in particular human hair.

These compounds are applied to the hair according to a process using a developing agent, the role of which is to produce dyeing of the fibres by reaction with the indole and/or indoline compound.

French Patents FR-1,133,594 and FR-1,166,172 and French Patent Application FR-A-2,659,229, the disclosures of which are incorporated herein by reference, provide processes for dyeing with the help of 5,6-dihydroxyindole or indole compounds, by using metal cations which act as a developing agent.

Manganese salts are mentioned among these metal cations. These manganese salts are used according to a two-step process which consists, in a first step, in applying the indole compound to the hair and in towel-drying and then, in a second step, in applying an alkaline solution containing a manganese salt to the hair. According to these documents, the indole compound can also be applied to the hair in the presence of an alkaline agent and, after rinsing, a solution containing a manganese salt can be applied.

These dyeing processes are not entirely satisfactory because the colourings obtained with the indole compounds used are not sufficiently intense. Moreover, some indole compounds cannot be developed by using these dyeing processes and consequently they do not lead to any dyeing of the hair.

In order to solve these problems, the Inventor has perfected the dyeing set which forms a subject of the invention.

A subject of the invention is therefore a set for dyeing keratinous fibres, and in particular human keratinous fibres such as hair, which comprises a combination of a dyeing composition (A) containing, in a medium appropriate for dyeing, at least one indole and/or indoline compound and at least one manganese salt, and a composition (B) containing, in a medium appropriate for dyeing, at least one basifying agent, wherein when the pH of the dyeing composition (A) is less than 7, the pH of the composition (B) is greater than 8.5 and, when the pH of the composition (A) ranges from 7 to 9, the pH of the composition (B) is greater than 9.5.

The pH of the dyeing composition (A) is preferably less than 7 and, in this case, the dyeing composition (A) is novel and constitutes another subject of the invention.

Another subject of the invention is a process for dyeing keratinous fibres, and in particular human keratinous fibres such as hair, using the dyeing set as defined above, which comprises, in a first step, applying the dyeing composition (A) to the keratinous fibres, and in a second step, applying the composition (B) to the keratinous fibres, under the following conditions:

(i): when the pH of the dyeing composition (A) is less than 7, the pH of the composition (B) is greater than 8.5 and (ii): when the pH of the dyeing composition (A) ranges from 7 to 9, the pH of the composition (B) is greater than 9.5.

The Inventor has discovered that, when the indole and/or indoline compound and the manganese salt are applied simultaneously to the hair, under the pH conditions described above, the hair colourings obtained are more intense than those of the prior art and they moreover have excellent resistance to the various treatments to which the hair may be subjected. Moreover, the dyeing process of the invention makes it possible to develop certain indole compounds, and in particular certain monohydroxyindoles, which could not be satisfactorily developed according to the processes of the state of the art.

The indole compounds which can be used in the dyeing composition (A) defined above correspond to formula (I):

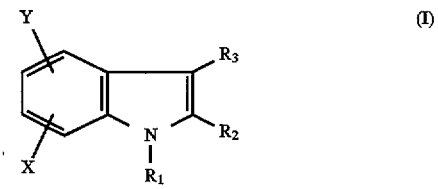

in which:

$R_1$ and $R_3$, which are identical or different, represent a hydrogen atom or a $C_1$–$C_4$ alkyl radical;

$R_2$ represents a hydrogen atom or a $C_1$–$C_4$ alkyl or —COOH radical;

X represents a hydrogen atom, $NH_2$, OH, a $C_1$–$C_4$ alkyl radical or a $C_1$–$C_4$ alkoxy radical; and Y represents OH or $NH_2$;

with the proviso that, when X represents OH or an alkyl radical, X occupies the 5, 6 or 7 positions and is in the ortho position with respect to Y; or a salt of the compound of formula (I).

Mention may be made, among the preferred indole compounds of formula (I), of 5,6-dihydroxyindole, 2-methyl-5, 6-dihydroxyindole, 3-methyl-5,6-dihydroxyindole, 4-hydroxyindole, 2,3-dimethyl-5,6-dihydroxyindole, 6-hydroxy-5-methoxyindole, 6-hydroxyindole, 5-hydroxyindole, 7-hydroxyindole, 7-aminoindole, 5-aminoindole, 5,6-dihydroxyindole-2-carboxylic acid, 4-aminoindole and 1-methyl-5,6-dihydroxyindole, or a salt of any of these compounds.

The indoline compounds which can be used in the dyeing composition (A) defined above correspond to formula (II):

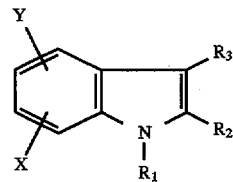

in which $R_1$, $R_2$, $R_3$, X and Y have the same meanings as those indicated above for the compounds of formula (I).

Mention may be made, among the preferred indoline compounds of formula (II), of 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline and 5-methoxy-6-hydroxyindoline, or a salt of any of these compounds.

According to the invention, the indole and/or indoline compounds are preferably present at a concentration which ranges from 0.05 to 10% by weight with respect to the total weight of the dyeing composition (A). More preferably still, this concentration ranges from 0.2 to 5% by weight with respect to the total weight of the dyeing composition (A).

The manganese salts which can be used in the dyeing composition (A) preferably have an oxidation number equal to 2 or 3, and are preferably chosen from manganese diacetate and its hydrates, such as, for example, manganese diacetate tetrahydrate, manganese dichloride and its hydrates, manganese sulphates, manganese carbonates, manganese dihydrogencarbonates, manganese acetylacetonate, manganese triacetate and its hydrates and manganese trichloride. Manganese diacetate tetrahydrate is particularly preferred.

According to the invention, the manganese salts are preferably present at a concentration which ranges from 0.002 to 5% by weight of metal equivalents with respect to the total weight of the dyeing composition (A). More preferably still, this concentration ranges from 0.05 to 2% by weight of metal equivalents with respect to the total weight of the dyeing composition (A).

According to a preferred embodiment of the invention, the dyeing composition (A) has a pH which ranges from 5 to 7.

The pH of the dyeing composition (A) can be adjusted to the desired value using conventional acidifying agents, among which there may preferably be mentioned, by way of example, orthophosphoric acid, lactic acid, acetic acid, tartaric acid, hydrochloric acid and citric acid.

The medium appropriate for dyeing is preferably an aqueous medium composed of water or a mixture of water and at least one organic solvent, the at least one organic solvent being used to dissolve the compounds which would be insufficiently soluble in water.

Mention may preferably be made, among these solvents, by way of example, of lower $C_1$-$C_4$ alkanols, such as ethanol and isopropanol; glycerol; glycols and glycol ethers such as 2-butoxyethanol, propylene glycol and the monoethyl ether and the monomethyl ether of diethylene glycol; aromatic alcohols such as benzyl alcohol and phenoxyethanol; analogous products and their mixtures.

When they are present, the solvents preferably represent from 1 to 40% by weight of the total weight of the dyeing composition (A) and more preferably still from 5 to 30% by weight.

The dyeing composition (A) may also contain at least one adjuvant chosen from the adjuvants conventionally used in compositions for dyeing the hair, such as anionic, cationic, non-ionic, amphoteric or zwitterionic surface-active agents, or mixtures thereof, inorganic or organic thickening agents, antioxidizing agents, penetrating agents, sequestering agents, fragrances, buffers, dispersing agents, conditioning agents, film-forming agents, preserving agents, opacifying agents, and the like.

The dyeing composition (A) can be provided in various forms, such as in the liquid, cream, gel, or foam form, or in any other form appropriate for carrying out dyeing of keratinous fibres and in particular of human hair.

The basifying agents present in the composition (B) applied in the second step are preferably chosen from conventional basifying agents such as, for example, aqueous ammonia, alkanolamines, such as, for example, mono-, di- and triethanolamines and their derivatives, sodium or potassium hydroxides such as, for example, sodium hydroxide and potassium hydroxide, alkylamines or alkali metal and ammonium carbonates. Monoethanolamine is particularly preferred.

The composition (B) containing the basifying agent can optionally contain an oxidizing agent, so as to accelerate the development of the indole and/or indoline compound.

This oxidizing agent can preferably be chosen from hydrogen peroxide, urea hydrogen peroxide, alkali metal bromates and persalts such as perborates and persulphates. Hydrogen peroxide is more preferably used, the assay of which preferably varies from 1 to 40 volumes, and more preferably varies from 3 to 20 volumes.

According to a preferred embodiment of the invention, the composition (B) containing the basifying agent contains an oxidizing agent when the indole compound of formula (I) present in the dyeing composition (A) is a monohydroxyindole.

According to a process of the invention, the dyeing composition (A) as defined above is applied to the hair with an exposure time preferably ranging from 1 to 30 minutes, and then the composition (B), containing the basifying agent, is applied with an exposure time preferably ranging from 1 to 30 minutes. According to a particularly preferred embodiment of the invention, the exposure time of each composition ranges from 5 to 20 minutes.

A towel-drying or rinsing step can, if desired, separate the application of the dyeing composition (A) from the application of the composition (B) containing the basifying agent.

The composition (B) containing the basifying agent can contain the same adjuvants as those defined for the dyeing composition (A) and can also be provided in various forms, such as those defined for the dyeing composition (A).

Another subject of the invention is a multi-compartment dyeing device, also known as a "dyeing kit" or "dyeing outfit", characterized in that it comprises at least two compartments, of which a first compartment contains the dyeing composition (A), as defined above, and a second compartment contains the composition (B) containing the basifying agent, also as defined above. Such devices are known per se.

The following examples are intended to illustrate the invention without limiting the scope thereof in any way.

DYEING EXAMPLES

EXAMPLES 1 to 4

The following compositions (A) and (B) were prepared:

| Composition (A): | |
| --- | --- |
| Ethanol | 10.0 g |
| Hydroxypropylated guar gum sold under the tradename Jaguar HP 60 by the company Mayhall | 0.8 g |
| Alkyl ($C_8$-$C_{10}$) polyglucoside as an aqueous solution containing 60% of active material (AM) buttered by ammonium citrate (0.5%), sold under the tradename Oramix C6110 by the company Seppic | 8 g |
| Compound of formula (I) and/or (II) | X g |
| Manganese diacetate tetrahydrate | 1 g |
| Demineralized water | q.s. for 100 g |
| Composition (B): | |
| Oleic acid diethanolamide | 0.8 g |
| Glycerol | 0.4 g |
| Mixture of cetylstearyl alcohol and of cetylstearyl alcohol polyoxyethylenated with 33 mol of ethylene oxide (80/20) sold under the tradename Dehsconet 390 by the company Tensia | 2 g |
| Monoethanolamine | 2 g |
| Hydrogen peroxide | N volumes |
| Demineralized water | q.s. for 100 g |

The composition (A) was applied for 15 minutes to natural grey hair containing 90% white hairs. After rinsing, the composition (B) was applied for 10 minutes. The hair was then rinsed and dried.

The results appear in the table below (contents in grams):

| EXAMPLE | 1 | 2 | 3 | 4 |
|---|---|---|---|---|
| Composition (A) | | | | |
| 5,6-dihydroxyindole | 1 | 1 | — | — |
| 4-hydroxyindole | — | — | 1 | — |
| 6-hydroxyindole | — | — | — | 1 |
| pH (A) | 6.5 | 6.5 | 6.5 | 6.5 |
| Composition (B) | | | | |
| Hydrogen peroxide (by volume) | — | 9 | 9 | 9 |
| pH (B) | 10.2 | 10.2 | 10.2 | 10.2 |
| Shade obtained | very dark grey | very dark grey | bluish ashen | matt golden |

COMPARATIVE EXAMPLES 5 to 10

EXAMPLE 5, Not Forming Part of the Invention

The following composition ($A_5$), which does not form part of the invention, i.e., is comparative, was prepared:

| | |
|---|---|
| Ethanol | 10.0 g |
| Hydroxypropylated guar gum sold under the tradename Jaguar HP 60 by the company Mayhall | 0.8 g |
| Alkyl ($C_8$–$C_{10}$) polyglucoside as an aqueous solution containing 60% of active material (AM) buffered by ammonium citrate (0.5%), sold under the tradename Oramix C6110 by the company Seppic | 8 g |
| 5,6-Dihydroxyindole | 1 g |
| Demineralized water | q.s. for 100 g |

The following composition ($B_5$), which does not form part of the invention, i.e., is comparative, was prepared:

| | |
|---|---|
| Oleic acid diethanolamide | 0.8 g |
| Glycerol | 0.4 g |
| Mixture of cetylstearyl alcohol and of cetyl-stearyl alcohol polyoxyethylenated with 33 mol of ethylene oxide (80/20) sold under the tradename Dehsconet 390 by the company Tensia | 2 g |
| Monoethanolamine | 2 g |
| Manganese diacetate tetrahydrate | 1 g |
| Demineralized water | q.s. for 100 g |

The composition ($A_5$) was applied to natural grey hair containing 90% white hairs for 15 minutes. The hair was then towel-dried and then the composition ($B_5$) was applied for 10 minutes. The hair was then rinsed and dried.

The results appear in the summarizing table found after Example 10.

EXAMPLE 6, Not Forming Part of the Invention

The following composition (A6), which does not form part of the invention, was prepared:

| | |
|---|---|
| Ethanol | 10.0 g |
| Hydroxypropylated guar gum sold under the tradename Jaguar HP 60 by the company Mayhall | 0.8 g |
| Alkyl ($C_8$–$C_{10}$) polyglucoside as an aqueous solution containing 60% of active material (AM) buffered by ammonium citrate (0.5%), sold under the tradename Oramix C6110 by the company Seppic | 8 g |
| 5,6-Dihydroxyindole | 1 g |
| Monoethanolamine | 2 g |
| Demineralized water | q.s. for 100 g |

The following composition ($B_6$), which does not form part of the invention, was prepared:

| | |
|---|---|
| Oleic acid diethanolamide | 0.8 g |
| Glycerol | 0.4 g |
| Mixture of cetylstearyl alcohol and of cetyl-stearyl alcohol polyoxyethylenated with 33 mol of ethylene oxide (80/20) sold under the tradename Dehsconet 390 by the company Tensia | 2 g |
| Manganese diacetate tetrahydrate | 1 g |
| Demineralized water | q.s. for 100 g |

The composition ($A_6$) was applied to natural grey hair containing 90% white hairs for 15 minutes. The hair was then rinsed and then the composition ($B_6$) was applied for 10 minutes. The hair was then rinsed.

The results appear in the summarizing table found after Example 10.

EXAMPLE 7, Not Forming Part of the Invention

The following composition ($A_7$), which does not form part of the invention, was prepared:

| | |
|---|---|
| Ethanol | 10.0 g |
| Hydroxypropylated guar gum sold under the tradename Jaguar HP 60 by the company Mayhall | 0.8 g |
| Alkyl ($C_8$–$C_{10}$) polyglucoside as an aqueous solution containing 60% of active material (AM) buffered by ammonium citrate (0.5%), sold under the tradename Oramix C6110 by the company Seppic | 8 g |
| 5,6-Dihydroxyindole | 1 g |
| Monoethanolamine | 2 g |
| Manganese diacetate tetrahydrate | 1 g |
| Demineralized water | q.s. for 100 g |

This example relates to a single-step process which does not form part of the invention.

The composition ($A_7$) was applied to natural grey hair containing 90% white hairs for 15 minutes and the hair was then rinsed and dried.

The results appear in the summarizing table found after Example 10.

EXAMPLE 8, Not Forming Part of the Invention

The following composition ($A_8$), which does not form part of the invention, was prepared:

| | |
|---|---|
| Ethanol | 10.0 g |
| Hydroxypropylated guar gum sold under the tradename Jaguar HP 60 by the company Mayhall | 0.8 g |
| Alkyl ($C_8$–$C_{10}$) polyglucoside as an aqueous solution containing 60% of active material (AM) buffered by ammonium citrate (0.5%), sold under the tradename Oramix C6110 by the company Seppic | 8 g |
| 5,6-Dihydroxyindole | 1 g |
| Demineralized water | q.s. for 100 g |

The following composition (B₈), which forms part of the invention, was prepared:

| | |
|---|---|
| Oleic acid diethanolamide | 0.8 g |
| Glycerol | 0.4 g |
| Mixture of cetylstearyl alcohol and of cetyl-stearyl alcohol polyoxyethylenated with 33 mol of ethylene oxide (80/29) sold under the tradename Dehsconet 390 by the company Tensia | 2 g |
| Hydrogen peroxide | 9 volumes |
| Monoethanolamine | 2 g |
| Demineralized water | q.s. for 100 g |

The composition (A₈) was applied to natural grey hair containing 90% white hairs for 15 minutes. The hair was then towel-dried and then the composition (B₈) was applied for 10 minutes. The hair was then rinsed and dried.

The results appear in the summarizing table found after Example 10.

EXAMPLE 9, Forming Part of the Invention

The following composition (A₉) was prepared:

| | |
|---|---|
| Ethanol | 10.0 g |
| Hydroxypropylated guar gum sold under the tradename Jaguar HP 60 by the company Mayhall | 0.8 g |
| Alkyl (C₈–C₁₀) polyglucoside as an aqueous solution containing 60% of active material (AM) buttered by ammoniuin citrate (0.5%), sold under the tradename Oramix C6110 by the company Seppic | 8 g |
| 5,6-Dihydroxyindole | 1 g |
| Manganese diacetate tetrahydrate | 1 g |
| Demineralized water | q.s. for 100 g |

The following composition (B₉) was prepared:

| | |
|---|---|
| Oleic acid diethanolamide | 0.8 g |
| Glycerol | 0.4 g |
| Mixture of cetylstearyl alcohol and of cetyl-stearyl alcohol polyoxyethylenated with 33 mol of ethylene oxide (80/20) sold under the tradename Dehsconet 390 by the company Tensia | 2 g |
| Monoethanolamine | 2 g |
| Demineralized water | q.s. for 100 g |

The composition (A₉) was applied for 15 minutes to natural grey hair containing 90% white hairs. After rinsing, the composition (B₉) was applied for 10 minutes. The hair was then rinsed and dried.

The results appear in the summarizing table found after Example 10.

EXAMPLE 10, Forming Part of the Invention

The following composition (A₁₀) was prepared: It was identical to the composition (A₉).

The following composition (B₁₀) was prepared: It was identical to the composition (B₉), except that it additionally contained 9 volumes of hydrogen peroxide.

The composition (A₁₀) was applied for 15 minutes to natural grey hair containing 90% white hairs. After rinsing, the composition (B₁₀) was applied for 10 minutes. The hair was then rinsed and dried.

The results appear in the summarizing table found below:

SUMMARIZING TABLE FOR EXAMPLES 5 to 10:

| EXAMPLE | pH Composition (A) | pH Composition (B) | COLOURING OBTAINED | | |
|---|---|---|---|---|---|
| | | | L | a | b |
| 5 (outside the invention | 6.5 | 10.2 | 26.8 | 0.3 | −0.5 |
| 6 (outside the invention | 6.5 | 10.2 | 27.9 | 0.3 | −0.6 |
| 7 (outside the invention | 6.5 | 10.2 | 33.8 | −0.6 | −0.2 |
| 8 (outside the invention) | 6.5 | 10.2 | 24.0 | 0.8 | 1.0 |
| 9 (according to the invention | 6.5 | 10.2 | 22.2 | 0.2 | 0.7 |
| 10 (according to the invention) | 6.5 | 10.2 | 22.0 | 0.2 | 0.5 |

The colour of the locks was evaluated in the (L) (a) (b) system.

According to this system, (L) indicates lightness. The higher the value of (L), the lighter the colour. Conversely, the lower the value of (L), the darker and therefore more intense the colour.

The hue and the saturation are expressed by (a) and (b). (a) and (b) indicate two colour axes, (a) the red/green axis and (b) the yellow/blue axis.

A positive value of (a) corresponds to a red hue which becomes more saturated as the absolute value of (a) increases.

A negative value of (a) corresponds to a green hue which becomes more saturated as the absolute value of (a) increases.

A positive value of (b) corresponds to a yellow hue which becomes more saturated as the absolute value of (b) increases.

A negative value of (b) corresponds to a blue hue which becomes more saturated as the absolute value of (b) increases.

Values close to zero for (a) or (b) correspond to grey hues.

The results obtained in Examples 5 to 10 show lower values for (L) for the dyeings carried out according to the process of the invention (Examples 9 and 10). The colourings obtained in Examples 9 and 10 are therefore more intense than those of Examples 5 to 8 according to the prior art.

What is claimed is:

1. A set for dyeing keratinous fibres, which comprises,
   a dyeing composition (A), wherein said dyeing composition (A) comprises, in a medium appropriate for dyeing, from 0.05 to 10% by weight with respect to the total weight of said dyeing composition (A) of at least one indole or indoline compound and from 0.002 to 5% by weight of metal equivalents with respect to the total weight of the dyeing composition (A) of at least one manganese salt which has an oxidation number equal to 2 or 3, and
   a composition (B), wherein said composition (B) comprises, in a medium appropriate for dyeing, at least one basifying agent and at least one oxidizing agent selected from the group consisting of hydrogen peroxide, urea hydrogen peroxide, an alkali metal bromate and a persalt, wherein said oxidizing agent is present in an amount effective to accelerate the development of said indole or indoline compound, wherein the pH of said dyeing composition (A) is less than 7, and the pH of said dyeing composition (B) is greater than 8.5, or wherein the pH of said dyeing composition (A) ranges from 7 to 9, and the pH of said composition (B) is greater than 9.5, and wherein said dyeing composition (A) and said composition (B) are present in an amount effective to dye said keratinous fibres.

2. A dyeing set according to claim 1, wherein said at least one indole compound present in said dyeing composition (A) is a compound of formula (I):

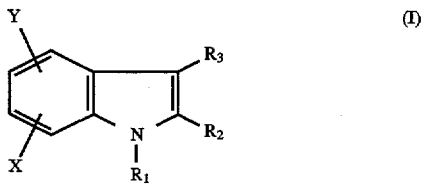

(I)

in which:

$R_1$ and $R_3$, which are identical or different, represent a hydrogen atom or a $C_1$–$C_4$ alkyl radical;

$R_2$ represents a hydrogen atom or a $C_1$–$C_4$ alkyl or —COOH radical;

X represents a hydrogen atom, $NH_2$, OH, a $C_1$–$C_4$ alkyl radical or a $C_1$–$C_4$ alkoxy radical; and Y represents OH or $NH_2$;

with the proviso that, when X represents OH or an alkyl radical, X occupies the 5, 6 or 7 position and is in the ortho position with respect to Y; or a salt of the compound of formula (I).

3. A dyeing set according to claim 2, wherein said at least one indole compound of formula (I) is 5,6-dihydroxyindole, 2-methyl-5,6-dihydroxyindole, 3-methyl-5,6-dihydroxyindole, 4-hydroxyindole, 2,3-dimethyl-5,6-dihydroxyindole, 6-hydroxy-5-methoxyindole, 6-hydroxyindole, 5-hydroxyindole, 7-hydroxyindole, 7-aminoindole, 5-aminoindole, 5,6-dihydroxyindole-2-carboxylic acid, 4-aminoindole, 1-methyl-5,6-dihydroxyindole, or a salt of any of said compounds.

4. A dyeing set according to claim 1, wherein said at least one indoline compound present in said dyeing composition (A) is a compound of formula (II):

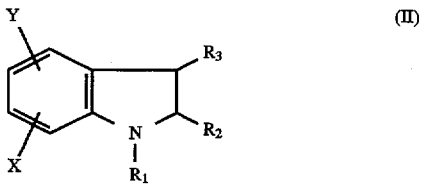

(II)

in which:

$R_1$ and $R_3$, which are identical or different, represent a hydrogen atom or a $C_1$–$C_4$ alkyl radical;

$R_2$ represents a hydrogen atom or a $C_1$–$C_4$ alkyl or —COOH radical;

X represents a hydrogen atom, $NH_2$, OH, a $C_1$–$C_4$ alkyl radical or a $C_1$–$C_4$ alkoxy radical; and Y represents OH or $NH_2$;

with the proviso that, when X represents OH or an alkyl radical, X occupies the 5, 6 or 7 position and is in the ortho position with respect to Y; or a salt of the compound of formula (II).

5. A dyeing set according to claim 4, wherein said at least one indoline compound of formula (II) is 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline, 5-methoxy-6-hydroxyindoline, or a salt of any of said compounds.

6. A dyeing set according to claim 1, wherein said at least one indole or indoline compound is present at a concentration which ranges from 0.2 to 5% by weight with respect to the total weight of said dyeing composition (A).

7. A dyeing set according to claim 1, wherein said at least one manganese salt is a manganese diacetate, a manganese diacetate hydrate, a manganese dichloride, a manganese dichloride hydrate, a manganese sulphate, a manganese carbonate, a manganese dihydrogencarbonate, a manganese acetylacetonate, a manganese triacetate, a manganese triacetate hydrate or a manganese trichloride.

8. A dyeing set according to claim 7, wherein said at least one manganese salt is manganese diacetate tetrahydrate.

9. A dyeing set according to claim 1, wherein said at least one manganese salt is present at a concentration which ranges from 0.05 to 2% by weight of metal equivalents with respect to the total weight of the dyeing composition (A).

10. A dyeing set according to claim 1, wherein said medium appropriate for dyeing is an aqueous medium comprising water or a mixture of water and at least one organic solvent.

11. A dyeing set according to claim 10, wherein said organic solvent is a lower $C_1$–$C_4$ alkanol, a glycerol, a glycol, a glycol ether, an aromatic alcohol, or a mixture of any of said solvents.

12. A dyeing set according to claim 1, wherein said at least one basifying agent is aqueous ammonia, an alkanolamine, sodium hydroxide, potassium hydroxide, an alkylamine, an alkali metal or an ammonium carbonate.

13. A dyeing set according to claim 12, wherein said at least one basifying agent is monoethanolamine.

14. A dyeing set according to claim 1, wherein said persalt is a perborate or a persulphate.

15. A dyeing set according to claim 1, wherein said oxidizing agent is hydrogen peroxide.

16. A dyeing set according to claim 2, wherein said composition (B) contains an oxidizing agent when the indole compound of formula (I) present in the dyeing composition (A) is a monohydroxyindole.

17. A dyeing set according to claim 1, wherein at least one of said dyeing composition (A) or said composition (B) is in liquid, cream, gel, foam, or any other form appropriate for carrying out said dyeing of said keratinous fibres.

18. A dyeing set according to claim 1, wherein said keratinous fibres are human keratinous fibres.

19. A dyeing set according to claim 18, wherein said human keratinous fibres are hair.

20. A process for dyeing keratinous fibres, which comprises the steps of:

(I) applying firstly to said keratinous fibres a dyeing composition (A), wherein said dyeing composition (A) comprises, in a medium appropriate for dyeing, from 0.05 to 10% by weight with respect to the total weight of said dyeing composition (A) of at least one indole or indoline compound and from 0.002 to 5% by weight of metal equivalents with respect to the total weight of the dyeing composition (A) of at least one manganese salt which has an oxidation number equal to 2 or 3;

(ii) applying secondly to said keratinous fibres a composition (B), wherein said composition (B) comprises, in a medium appropriate for dyeing, at least one basifying agent and at least one oxidizing agent selected from the group consisting of hydrogen peroxide, urea hydrogen peroxide, an alkali metal bromate and a persalt, wherein said oxidizing agent is present in an amount effective to accelerate the development of said indole or indoline compound; and (iii) subsequently rinsing said keratinous fibres;

wherein the pH of said dyeing composition (A) is less than 7, and the pH of said composition (B) is greater than 8.5, or wherein the pH of said dyeing composition (A) ranges from 7 to 9, and the pH of said composition (B) is greater than 9.5 and wherein said composition (A) and said composition (B) are present in an amount effective to dye said keratinous fibres.

21. A process according to claim 20, wherein said dyeing composition (A) is applied to said keratinous fibres for an exposure time ranging from 1 to 30 minutes, and said composition (B) is applied to said keratinous fibres for an exposure time ranging from 1 to 30 minutes.

22. A process according to claim 21, wherein said exposure time for said dyeing composition (A) and said composition (B) each ranges from 5 to 20 minutes.

23. A process according to claim 20, wherein a towel-drying or a rinsing step separates the application of the dyeing composition (A) from the subsequent application of the composition (B).

24. A multi-compartment dyeing kit, which comprises at least two compartments, wherein a first compartment contains a dyeing composition (A) and a second compartment contains a composition (B), said compositions (A) and (B) being defined according to claim 1.

25. A process according to claim 20, wherein said keratinous fibres are human keratinous fibres.

26. A process according to claim 25, wherein said human keratinous fibres are hair.

* * * * *